United States Patent
Lint et al.

(10) Patent No.: US 9,582,995 B2
(45) Date of Patent: Feb. 28, 2017

(54) METHOD OF SELECTIVELY PAIRING WIRELESS CONTROLLER TO MULTIPLE DENTAL/MEDICAL INSTRUMENTS

(71) Applicants: Kevin Kenneth Lint, Seven Valleys, PA (US); Joseph Robert Reagan, Steelton, PA (US)

(72) Inventors: Kevin Kenneth Lint, Seven Valleys, PA (US); Joseph Robert Reagan, Steelton, PA (US)

(73) Assignee: Dentsply International Inc., York, PA (US)

( * ) Notice: Subject to any disclaimer, the term of this patent is extended or adjusted under 35 U.S.C. 154(b) by 0 days.

(21) Appl. No.: 13/775,568

(22) Filed: Feb. 25, 2013

(65) Prior Publication Data

US 2014/0062662 A1    Mar. 6, 2014

Related U.S. Application Data

(63) Continuation of application No. 13/084,945, filed on Apr. 12, 2011, now abandoned.
(Continued)

(51) Int. Cl.
*G08C 19/00* (2006.01)
*A61C 1/00* (2006.01)
(Continued)

(52) U.S. Cl.
CPC ............ *G08C 19/00* (2013.01); *A61C 1/0015* (2013.01); *A61C 1/0023* (2013.01); *G05G 1/46* (2013.01); *A61B 2017/00225* (2013.01)

(58) Field of Classification Search
CPC ... H04W 12/06; H04W 4/26; H04W 52/0209; H04L 63/08; H04L 67/22;
(Continued)

(56) References Cited

U.S. PATENT DOCUMENTS

| 4,156,187 A | 5/1979 | Murry et al. |
| 4,171,572 A | 10/1979 | Nash |

(Continued)

FOREIGN PATENT DOCUMENTS

WO    2005060859 A1    7/2005

OTHER PUBLICATIONS

International Search Report, application 2011/032083, published Apr. 12, 2011.
(Continued)

*Primary Examiner* — Dustin Nguyen
*Assistant Examiner* — Juan C Turriate Gastulo
(74) *Attorney, Agent, or Firm* — Leana Levin; Dougles J. Hurq; David A. Zdurne

(57) ABSTRACT

In a dental operatory system a master device coordinates the activity levels of multiple slave devices. The master device coordinates activity via a communication link with all slave devices. A communication protocol incorporates a closed system addresses scheme in which the master device learns all associated addresses of slave devices, and all slave devices learn all associated addresses of the master device. Each communication between master device and any slave device includes both the master device address and the slave device address. The master device scans all slave devices for an activity status and determines which slave device exhibits a threshold level of activity, and whether activity is increasing or decreasing. The master device passes a communication control token to the slave device to be controlled by operation of the master device.

17 Claims, 1 Drawing Sheet

Related U.S. Application Data

(60) Provisional application No. 61/323,142, filed on Apr. 12, 2010, provisional application No. 61/323,129, filed on Apr. 12, 2010, provisional application No. 61/323,159, filed on Apr. 12, 2010, provisional application No. 61/323,120, filed on Apr. 12, 2010.

(51) Int. Cl.
*G05G 1/46* (2008.04)
*A61B 17/00* (2006.01)

(58) Field of Classification Search
CPC ............... A61C 1/0015; A61C 1/0023; A61B 2017/00225; G08C 19/00; G05G 1/46
USPC .................................................. 709/208, 226
See application file for complete search history.

(56) References Cited

U.S. PATENT DOCUMENTS

| | | | |
|---|---|---|---|
| 4,305,126 A | 12/1981 | Beier et al. | |
| 4,571,681 A | 2/1986 | Beier et al. | |
| 5,931,669 A | 8/1999 | Fornoff et al. | |
| 5,970,457 A | 10/1999 | Brant et al. | |
| 7,625,208 B2 | 12/2009 | Warner | |
| 7,659,833 B2 | 2/2010 | Warner et al. | |
| 7,675,430 B2 | 3/2010 | Warner et al. | |
| 2002/0135474 A1* | 9/2002 | Sylliassen | 340/540 |
| 2003/0232305 A1* | 12/2003 | Warner | 433/98 |
| 2004/0002704 A1 | 1/2004 | Knowlton et al. | |
| 2004/0230262 A1 | 11/2004 | Sartor et al. | |
| 2005/0076122 A1* | 4/2005 | Khawand et al. | 709/226 |
| 2005/0080403 A1* | 4/2005 | Takahashi | 606/1 |
| 2007/0274240 A1* | 11/2007 | Weidenhaupt et al. | 370/310 |
| 2008/0189381 A1* | 8/2008 | Poirier | 709/208 |
| 2011/0002003 A1* | 1/2011 | Suwabe | 358/1.14 |
| 2011/0216016 A1* | 9/2011 | Rosener | G06F 3/041 345/173 |

OTHER PUBLICATIONS

International Written Opinion, application 2011/032083, published Apr. 12, 2011.

\* cited by examiner

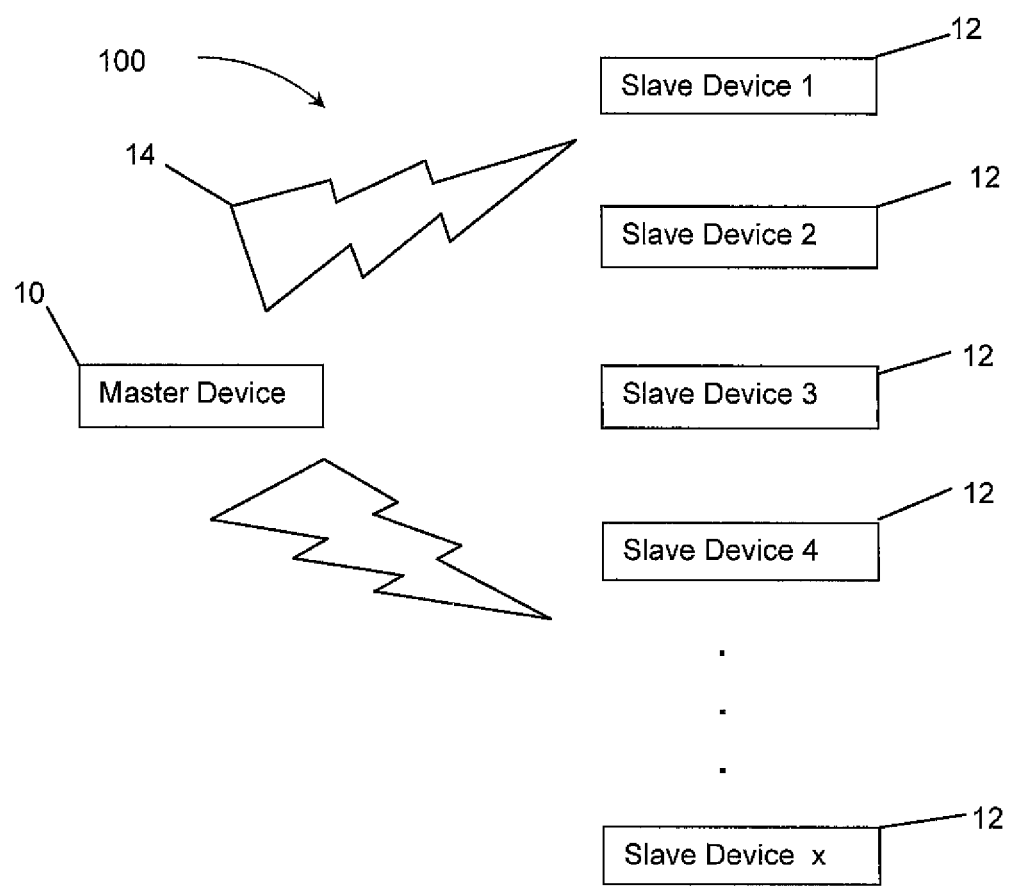

METHOD OF SELECTIVELY PAIRING WIRELESS CONTROLLER TO MULTIPLE DENTAL/MEDICAL INSTRUMENTS

This application claims priority to and the benefit of U.S. Provisional Patent Application No. 61/323,142 filed Apr. 12, 2010; U.S. Provisional Patent Application No. 61/323,129 filed Apr. 12, 2010; U.S. Provisional Patent Application No. 61/323,159 filed Apr. 12, 2010; and U.S. Provisional Patent Application No. 61/323,120 filed Apr. 12, 2010 all of which are hereby incorporated by reference in their entirety.

FIELD OF THE INVENTION

The present invention is directed to a method and system for wirelessly controlling multiple medical devices from a shared control device, and more particularly, to a footswitch or pedal having embedded software to allow selective control one or more dental or medical devices.

BACKGROUND OF THE INVENTION

Dental and medical professionals use many instruments that are controlled by foot control systems. For example, surgical cutting instruments, endoscopic tools, irrigation and aspiration tools, dental drills and other handpieces, ultrasonic dental scalers, and dental prophylaxis units can be activated with foot control systems. The foot control system typically includes a foot pedal device that is placed on the floor within easy reach of the practitioner. The foot pedal is used to activate a dental/medical apparatus, which includes a base-operating unit. The foot pedal is typically connected to the base unit by a connector cable in a "hard-wired" system.

Alternatively, remote, "wireless" foot control systems, which do not use a connector cable, can be used to activate the base unit in some instances. In such arrangements, a flexible instrument cable connects the dental/medical instrument, for example, a dental handpiece, to the base unit. The dental or medical practitioner activates the base unit and attached dental/medical instrument by depressing the foot pedal with his or her foot.

Some conventional foot pedals are referred to as multi-position or multi-staged switches. An operator depresses the pedal of the foot pedal to a certain position, and this action causes the dental/medical apparatus to operate in a specific mode. The particular operational mode is based on the position of the foot pedal. For example, with a two-position foot pedal, a dental practitioner can depress the pedal to a first position so that water flows through the handpiece for rinsing the teeth of a patient. Then, the pedal of the foot pedal can be depressed to a second position so that a cleaning spray flows through the handpiece for cleaning the teeth. Such foot control systems provide several advantages.

First, the foot pedal device is easy to use and efficient. The dental/medical professional can activate the instrument attached to the base unit by simply depressing the foot pedal with his or her foot. Secondly, the dental/medical practitioner's hands are kept free when working with a foot pedal device. The practitioner thus can handle other instruments and accessories while treating the patient. The practitioner is better able to concentrate on performing the needed dental/medical procedure. Thirdly, as mentioned above, some conventional foot pedals are used in wireless systems, which do not run a connector cable between the foot pedal and base unit. These wireless foot pedals are used to remotely activate the base unit and attached dental/medical instruments. Many dental/medical operatory rooms contain numerous long cords, cables, wires, and the like which can become entangled easily. The entangled cords and cables take up space and may cause potential safety hazards. A wireless foot pedal system helps minimize some of these hazards.

Existing controllers may employ a single foot pedal to control multiple devices. Such an arrangement generally requires the use of an internal switch board or a gating system mounted within the foot pedal to permit the user to select the desired device, e.g., by entering a unique code, that is to be controlled by the foot pedal. This proposed control methodology eliminates the need for a user to use a switch board or gating system to select the desired instrument which is being controlled and instead the selection is made automatically as the user picks up the desired instrument.

Foot pedal functions are not readily reconfigurable, and modifying the function of existing foot pedals can be a time consuming and complex operation. Reconfiguring a foot pedal typically requires a custom mechanical assembly or unique switch contact selection that changes the operating mode of the associated foot pedal.

SUMMARY OF THE INVENTION

In one aspect there is a system for controlling a plurality of devices. The system includes a master device and a plurality of slave devices. The master device is configured to control one slave device selected from the plurality of slave devices. A communication protocol is configured with a predetermined addressing scheme in which the master device is configured to learn an address associated with each slave device. Each slave device is configured to learn the address of the master device, and the master device is configured to learn the address of each slave device. In the alternative, each slave device is configured to learn all addresses associated with each slave device and of the master device. A communication between the master device and the one slave device includes both the master device address and the slave device address. The communication protocol configured to request an activity level from each of the plurality of slave devices, determine which slave device of the plurality of slave devices exhibits a predetermined threshold level of activity, select the one slave device having the predetermined threshold level of activity, and control the one slave device by the master device.

In another aspect, there is a method of controlling a plurality of devices. The method includes providing a master device and a plurality of slave devices; associating an address with each slave device and the master device; learning all addresses associated with each slave device and of the master device; communicating between the master device and at least one slave device includes both the master device address and the slave device address; requesting an activity level from each of the plurality of slave devices; determining which slave device of the plurality of slave devices exhibits a predetermined threshold level of activity; selecting one slave device having the predetermined threshold level of activity; and controlling the selected slave device by the master device.

BRIEF DESCRIPTION OF THE DRAWINGS

FIG. 1 shows a schematic diagram of an exemplary control system including master devices and slave devices.

DETAILED DESCRIPTION OF THE INVENTION

An automatic device sense and selection wireless foot pedal controller for wireless devices includes a remote foot pedal, two or more medical or dental devices. Each of the medical or dental devices, which are referred to herein generally as slave devices, is configured with hardware or software, or a combination thereof, to communicate wirelessly with a master device or controller, e.g., a remote foot pedal; each having an activity sensor incorporated into the handpiece or handpiece portion of the slave device. The activity sensors determine an activity level of the associated slave device, e.g., a handpiece, when the slave device is picked up. Devices which may be suitable for sensing activity such as the movement of a slave device include by way of example and not limitation, any of the following sensors: tilt switches, sensitivity switches, accelerometers in single, dual, or tri axial configurations, heat sensors, capacitive touch sensors, inductive touch sensors, resistive touch sensors, proximity sensors, and combinations thereof.

In at least one exemplary embodiment a remote foot pedal is designated as the master device 10. Master device 10 coordinates the activity levels of multiple slave devices 12 associated with master device 10. In other embodiments, any of the slave devices 12 which are active during every use may be designated as the master device. All of the remaining active devices are configured as slave devices 12. Master device 10 coordinates activity via a communication link, indicated by arrows 14 generally, with all slave devices 12 which are powered on and may be available for use. A communication protocol incorporates a closed system addresses scheme in which master device 10 learns all associated addresses of slave devices 12, and all slave devices learn all associated addresses of master device 10. Each communication between master device 10 and any slave device 12 includes both the master device address and the slave device address. Upon initiation of operation, e.g., the foot pedal device, is actuated, master device 10 first scans all slave devices 12, and requests an activity status from each of slave devices 12 which are awake, i.e., currently capable of communicating with master device 10. Once master device 10 receives activity levels from each active slave device 12, master device 10 evaluates the activity status information received of each slave device 12 to determine which slave device 12 exhibits a threshold level of activity in the respective slave devices 12, and further determines whether the device activity level is increasing or decreasing. Master device 10 selects which of the active slave devices 12 best meets the activity status criteria, and passes a communication control token allowing the selected slave device 12 to be controlled by operation of, e.g., the foot pedal serving as master device 10. The foot pedal will now communicate solely with the selected slave device 12 until a new slave device 12 is selected. A new slave device 12 may be selected when the operatory system 100 has been inactive for a predetermined time out (i.e., time since the foot pedal was last actuated). Once the predetermined time has expired, master device 10 must start the initialization process again to determine which is the most active slave device 12 in the system 100 through the initialization process described above. For example, after an extended interval with no activity, a dentist may pick up a handpiece. Master device 10—e.g., the foot pedal—will determine that the handpiece is the most recently activated slave device 12, and that the activity level of the handpiece has increased. Thus master device 10 will automatically select the handpiece for control communications by passing the communication token to the handpiece. When the foot pedal is subsequently actuated, typically by depressing an actuator member on the foot pedal, control signals are sent from the foot pedal to the handpiece, which is the only slave device 12 that will respond to the control signals that follow from the foot pedal.

The activity level includes at least two pieces of information. The first piece of information is a number which represents the amount of activity a slave device has encountered over a set period of time. This number is a time averaged weighted value over a predetermined time interval. The second piece of information is the derivative of the time weighted average. This information allows knowledge of the direction of activity, i.e., if the activity level is increasing or decreasing and at what rate the activity level is changing. These activity levels may be determined by a multitude of sensors which are activated by either the touch or near touch of a hand or by the detection of motion such as when a handpiece is picked up for use.

Foot pedal software is used to reconfigure the foot pedal at the command of the user, rather than using custom mechanical assemblies or switch contact selections to change the mode of operation of the foot pedal. The software solution reduces the time and complexity of reconfiguring the foot pedal operation.

The foot pedal is configured to permit the user to select the slave device 12 and control the slave device 12 in a stepped mode of operation. The stepped mode of operation comprises two or more modes in which to operate slave device 12. Slave device 12 can also be utilized in a continuous mode of operation. In continuous mode the foot pedal may control the speed of a handpiece, increasing speed as more pressure is applied to the foot pedal and decreasing speed as pressure is removed from the device. The next mode of operation would allow the foot pedal to change the range of performance of the device it controls, e.g. changing the speed range from 200 to 2500 rpm to 200 to 5000 rpm. This change would be accomplished by tapping the foot pedal in a specified pattern or sequence to change the mode of operation of the device. The foot pedal could have multiple modes of operation programmed into the device, allowing the user to select through a selection of preprogrammed options. A final mode of operation of the foot pedal may be a learning mode in which the user selects a minimum speed and a maximum speed, thereby programming into the foot pedal software the range of interest of the slave device. The foot pedal may be used to control the speed of a hand piece, power range of an ultrasonic scaler, powder delivery of an air polishing system or foot-operated control of any other dental device.

The foot pedal configuration incorporates complex functionality into a simplified method of mode selection. The user may switch between different ranges of performance easily, by selecting the program feature and choosing the range of interest. This selection is accomplished without the use of a tool. It also allows the user to change the foot pedal configuration without performing complex instructions or physically changing the setting of the device. The user is thus provided with a method to modify the foot pedal performance easily in real-time without disrupting a procedure or removing the medical professional's attention from the patient.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A system for controlling a plurality of devices, the system comprising:
  a master device and a plurality of slave devices; the master device configured to control one slave device selected from the plurality of slave devices;
  a communication protocol configured with a predetermined addressing scheme in which the master device is configured to learn an address associated with each slave device, and each slave device is configured to learn all addresses associated with each slave device and of the master device; wherein a communication between the master device and the one slave device includes both the master device address and the slave device address; the communication protocol configured to:
    request an activity level from each of the plurality of slave devices;
    determine which slave device of the plurality of slave devices exhibits a predetermined threshold level of activity;
    select the one slave device having the predetermined threshold level of activity; and
    control the one slave device by the master device wherein the master device is a foot pedal;
  wherein the activity level includes at least a first piece of information and a second piece of information;
  the first piece of information comprising a number representing a level of activity a corresponding slave device has encountered over a predetermined interval; and
  the second piece of information comprising a derivative of a time weighted average representing a direction of the level of activity;
  wherein the activity levels are determined by at least one sensor which is activated by a touch or a near touch of a hand or by a detection of motion; and
  wherein the number comprises a time averaged weighted value over a predetermined time interval; and
  wherein the time weighted average makes it possible to determine an average duration of time the slave device is utilized.

2. The system of claim 1, wherein the communication protocol is further configured to coordinate an activity level of multiple slave devices associated with the master device via a communication link.

3. The system of claim 1, wherein the predetermined addressing scheme is a closed system addressing scheme.

4. The system of claim 1, wherein the communication protocol is embedded in the master device.

5. The system of claim 1, wherein the communication protocol is configured to request the activity level from each of the plurality of slave devices by performing a scan of the plurality of slave devices.

6. The system of claim 5, wherein the communication protocol is further configured to evaluate the activity level received of each slave device.

7. The system of claim 6, wherein the communication protocol is further configured to determine whether the activity level of each slave device is increasing or decreasing in the respective slave device in response to the determined activity level.

8. The system of claim 1, wherein the communication protocol is further configured to select one slave device of the plurality of slave devices which meets a predetermined activity level criteria; and pass from the master device to the selected slave device a communication control token.

9. The system of claim 8, wherein the communication protocol is further configured to control slave device until a new slave device is selected.

10. A method of controlling a plurality of devices, comprising:
  providing a master device and a plurality of slave devices;
  associating an address with each slave device and the master device;
  learning all addresses associated with each slave device and of the master device;
  communicating between the master device and at least one slave device includes both the master device address and the slave device address; wherein the communication involves a predetermined addressing scheme in which the master device is configured to learn an address associated with each slave device, and each slave device is configured to learn all addresses associated with each slave device and of the master device;
  requesting an activity level from each of the plurality of slave devices;
  determining which slave device of the plurality of slave devices exhibits a predetermined threshold level of activity;
  selecting one slave device having the predetermined threshold level of activity; and
  controlling the selected slave device by the master device, wherein the master device is a foot pedal;
  associating with the activity level at least a first piece of information and a second piece of information;
  determining each respective activity level by at least one sensor which is activated by a touch or a near touch of a hand or by a detection of motion;
  representing by a number a level of activity a slave device has encountered over a predetermined interval; and
  deriving a time weighted average representing a direction of the level of activity; and determining a time averaged weighted value of activity level over a predetermined time interval; and assigning the number based on the time averaged weighted value wherein the time weighted average makes it possible to determine an average duration of time the slave device is utilized.

11. The method of claim 10, further comprising coordinating an activity level of multiple slave devices associated with the master device via a communication link.

12. The method of claim 10, wherein associating an address comprises a closed method addressing scheme.

13. The method of claim 10, further comprising scanning of the plurality of slave devices and requesting the activity level from each of the plurality of slave devices.

14. The method of claim 13, further comprising evaluating the activity level received of each slave device.

15. The method of claim 14, further comprising determining whether the activity level of each slave device is increasing or decreasing in the respective slave device.

16. The method of claim 15, further comprising selecting one slave device of the plurality of slave devices which meets a predetermined activity level criteria; and passing a communication control token from the master device to the selected slave device.

17. A system for controlling a plurality of devices, the system comprising:
   a master device and a plurality of slave devices; the master device configured to control one slave device selected from the plurality of slave devices;
   a communication protocol configured with a predetermined addressing scheme in which the master device is configured to learn an address associated with each slave device, and each slave device is configured to learn all addresses associated with each slave device and of the master device; wherein a communication between the master device and the one slave device includes both the master device address and the slave device address; the communication protocol configured to:
   request an activity level from each of the plurality of slave devices;
   determine which slave device of the plurality of slave devices exhibits a predetermined threshold level of activity;
   select the one slave device having the predetermined threshold level of activity;
   associate with the activity level at least a first piece of information and a second piece of information;
   determine each respective activity level by at least one sensor which is activated by a touch or a near touch of a hand or by a detection of motion;
   represent by a number a level of activity a slave device has encountered over a predetermined interval; and
   derive a time weighted average representing a direction of the level of activity;
   and determining a time averaged weighted value of activity level over a predetermined time interval; wherein the time weighted average makes it possible to determine an average duration of time the slave device is utilized
   assign the number based on the time averaged weighted value; and
   control the one slave device by the master device, wherein the master device is a foot pedal.

* * * * *